United States Patent [19]
Preissman

[11] Patent Number: 6,033,411
[45] Date of Patent: Mar. 7, 2000

[54] PRECISION DEPTH GUIDED INSTRUMENTS FOR USE IN VERTEBROPLASTY

[75] Inventor: Howard Preissman, San Jose, Calif.

[73] Assignee: Parallax Medical Inc., Mountain View, Calif.

[21] Appl. No.: 08/949,839

[22] Filed: Oct. 14, 1997

[51] Int. Cl.$^7$ .................................................... A61B 17/58
[52] U.S. Cl. .............................. 606/99; 604/164; 604/165
[58] Field of Search ................................. 606/61, 73, 72, 606/60, 86, 79, 92, 93, 94, 95, 102, 169–180, 99; 604/164, 165, 166, 167

[56] References Cited

U.S. PATENT DOCUMENTS

| | | |
|---|---|---|
| 4,469,109 | 9/1984 | Mehl . |
| 4,670,008 | 6/1987 | Von Albertini . |
| 4,793,363 | 12/1988 | Ausherman et al. . |
| 5,014,717 | 5/1991 | Lohrmann . |
| 5,195,526 | 3/1993 | Michelson . |
| 5,372,583 | 12/1994 | Roberts et al. . |
| 5,456,267 | 10/1995 | Stark . |
| 5,458,579 | 10/1995 | Chodorow et al. . |
| 5,660,186 | 8/1997 | Bachir . |

FOREIGN PATENT DOCUMENTS 44 13 520 A1  10/1995  Germany .

OTHER PUBLICATIONS

Cotten et al., "Preoperative percutaneous injection of methyl methacrylate and N–butyl cyanoacrylate in vertebral hemangiomas" *Am J Neuroradiol* (1996) 17:137–142.

Cybulski, "Methods of surgical stabilization for metastatic disease of the spine" *Neurosurgery* (1989) 25:240–252.

Deramond et al., "Percutaneous vertebroplasty with methyl–methyacrylate: technique, method, results" *Radiology* (1990) 117(supp.):352.

Galibert et al., "Note préliminaire sur le traitement des angiomes vertébraux par vertébroplastie acrylique percutanée" *Neurochirurgie* (1987) 33:166–168. (Partial summary translation included).

Harrington, "Anterior decompression and stabilization of the spine as a treatment for vertebral collapse and spinal cord compression from metastatic malignancy" *Clinical Orthodpaedics and Related Research* (1988) 233:177–197.

Kaemmerlen et al., "Vertébroplastie percutanée dans le traitement des métastases" *J. Radiol.* (1989) 70(10):557–562. (Partial summary translation included).

Nicola et al., "Vertebral hemangioma: Retrograde embolization—Stabilization with methyl methacrylate" *Surg Neurol* (1987) 27:481–486.

O'Donnell et al., "Recurrence of giant–cell tumors of the long bones after curettage and packing with cement" *J. of Bone and Joint Surg* (1994) 76–A(12):1827–1833.

(List continued on next page.)

*Primary Examiner*—Michael Buiz
*Assistant Examiner*—Lien Ngo
*Attorney, Agent, or Firm*—Morrison & Foerster LLP

[57] ABSTRACT

Precision depth guided instruments are provided for use in performing percutaneous implantation of hard tissue implant materials. A depth guided stylet include a point adapted for piercing hard tissue, and preferably, self-tapping threads for self-tapping into hard tissue. The stylet may include an elongated rod having a first section having a first diameter, and a second section having a second diameter larger than the first diameter. A cannula for use with a depth guided stylet includes an elongated tube having first and second open ends adapted for a depth guided stylet to pass therethrough. The cannula may include a pawl passing through the elongated tube for ratcheting against a rack of gear teeth provided on the stylet. Alternatively, a camming mechanism may be pivotal arranged on the stylet. Upon pivoting the camming mechanism, the cam surface provides a driving force against the cannula to drive the cannula along the stylet. A method of using the instruments is also disclosed, as is a kit which includes the instruments and which is used to open a pathway into hard tissue.

15 Claims, 12 Drawing Sheets

OTHER PUBLICATIONS

Persson et al., "Favourable results of acrylic cementation for giant cell tumors" *Acta Orthop Scand* (1984) 55:209–214.

Shapiro, "Cranioplasty, vertebral body replacement, and spinal fusion with tobramycin–impregnated methylmethacrylate" *Neurosurgery* (1991) 28(6):789–791.

Stringham et al., "Percutaneous transpedicular biopsy of the spine" *Spine* (1994) 19(17):1985–1991.

Sundaresan et al., "Treatment of neoplastic epidural cord compression by vertebral body resection and stabilization" *J. Neurosurg* (1985) 63:676–684.

Wang et al., "Safety of anterior cement fixation in the cervical spine: In vivo study of dog spine" *So. Medical J.* (1984) 77(2):178–179.

Weill et al., "Spinral metastases: Indications for and results of percutaneous injection of acrylic surgical cement" *Radiology* (1996) 199(1):241–247.

"Trocar Entry Control" *Research Disclosure*, No. 38938, pp. 570–574 (Sep. 1996).

PRECISION DEPTH GUIDED INSTRUMENTS FOR USE IN VERTEBROPLASTY

CROSS-REFERENCE TO RELATED APPLICATIONS

The present application is related to a copending application, Ser. No. 08/950,382 filed on Oct. 14, 1997.

TECHNICAL FIELD

The present invention relates to instruments for more accurately controlling the placement thereof, during surgical procedures for the repair of hard tissue by injection of hard tissue implant materials. Procedures for such repair include hip augmentation, mandible augmentation, and particularly vertebroplasty, among others.

BACKGROUND ART

Polymethylmethacrylate (PMMA) has been used in anterior and posterior stabilization of the spine for metastatic disease, as described by Sundaresan et al., "Treatment of neoplastic epidural cord compression by vertebral body resection and stabilization." *J Neurosurg* 1985;63:676–684; Harrington, "Anterior decompression and stabilization of the spine as a treatment for vertebral collapse and spinal cord compression from metastatic malignancy." *Clinical Orthodpaedics and Related Research* 1988;233:177–197; and Cybulski, "Methods of surgical stabilization for metastatic disease of the spine." *Neurosurgery* 1989;25:240–252.

Deramond et al., "Percutaneous vertebroplasty with methyl-methacrylate: technique, method, results [abstract]." *Radiology* 1990;117 (suppl):352; among others, have described the percutaneous injection of PMMA into vertebral compression fractures by the transpedicular or paravertebral approach under CT and/or fluoroscopic guidance. Percutaneous vertebroplasty is desirable from the standpoint that it is minimally invasive, compared to the alternative of surgically exposing the hard tissue site to be supplemented with PMMA or other filler.

The general procedure for performing percutaneous vertebroplasty involves the use of a standard 11 gauge Jamshidi needle. The needle includes an 11 gauge cannula with an internal stylet. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone.

A large force must be applied by the user, axially through the Jamshidi needle to drive the stylet through the cortical bone. Once penetration of the cortical bone is achieved, additional downward axial force, but at a reduced magnitude compared to that required to penetrate the cortical bone, is required to position the stylet/tip of the cannula into the required position within the cancellous bone. If the force magnitude is not reduced appropriately, or if very soft bone is encountered, as is often the case with osteoporitic patients, the stylet and cannula can be accidentally and suddenly driven through the cortical bone on the opposite side of the vertebra. This is a very dangerous and potentially lethal situation in the case of vertebroplasty, since the aorta is located in close proximity to the anterior surface of at least the thoracic and lumbar vertebrae, and could easily be punctured by such an occurrence. Additionally, with regard to all vertebrae, the spinal cord is located medially of the pedicle, and could also be damaged by a piercing stylet.

Accordingly, there exists a need for a more controlled approach to the interior of a vertebral body for the performance of vertebroplasty and particularly, percutaneous vertebroplasty.

DISCLOSURE OF THE INVENTION

Disclosed are instruments for percutaneously accessing hard tissue to deliver a hard tissue implant material thereby. A depth guided stylet includes an elongated rod having first and second ends and a longitudinal axis. The first end terminates in a point adapted for piercing hard tissue. A handle is provided on the second end of the elongated rod for providing a mechanical advantage to a user in rotating the elongated rod about the rod's longitudinal axis.

Self-tapping threads preferably extend from the point along the elongated rod for a predetermined distance. The self-tapping threads are adapted to self-tap into hard tissue. A rack of gear teeth may be provided on the elongated rod in a location between the self-tapping threads and the second end of the elongated rod.

A cannula for use with a depth guided stylet is disclosed as including an elongated tube having first and second open ends adapted for a depth guided stylet to pass therethrough A pawl may extend through the elongated tube, for ratcheting with the gear teeth on the depth guiding stylet. A handle is attached to the second end of the elongated tube.

A kit for open a pathway into hard tissue, includes a depth guided stylet and a cannula according to the present invention. The kit may include a stylet having an elongated rod terminating in a point adapted for piercing hard tissue, and gear teeth located along the elongated rod, in which case the cannula may include an elongated tube having first and second open ends for allowing the depth guided stylet to pass therethrough, and a pawl extending through the elongated tube and adapted to ratchet with the gear teeth of the stylet Alternatively, the kit may include a stylet having an elongated rod terminating in a point adapted for piercing hard tissue, and a camming mechanism pivotally mounted to provide a driving force to the cannula upon rotation thereof. In this case, the cannula includes an elongated tube having first and second open ends adapted for allowing the stylet to pass therethrough, and a surface adapted to interact with the camming mechanism for the transfer of the driving force.

In any case, the stylet preferably further includes self-tapping threads extending from the point along the elongated rod for a predetermined distance, which are adapted to self-tap into hard tissue. Further, a handle is provided on the second end of the stylet for providing a mechanical advantage to a user in rotating the elongated rod about its longitudinal axis. Likewise, a handle is provided on the second end of the elongated tube of the cannula.

Further, a connector is provided on the cannula handle for connecting the cannula to tubing following removal of the stylet from within the cannula. Alternatively, the connector may be arranged with an additional bore in the handle that allows connection with tubing and the commencement of injection of implant material before the stylet is completely removed from the cannula. Preferably the connector comprises a Luer lock fitting.

Another aspect of the present invention is the provision of a cannula having an elongated tube with a first section having a first diameter, and a second section having a second diameter larger than diameter of the first section, to reduce the pressure requirements for effectively injecting the implant material. Additionally, the elongated rod of the stylet may be provide with a first rod section having a first rod diameter, and a second rod section having a second rod diameter larger than the first rod diameter, to closely follow the contour of the cannula.

A method of percutaneously implanting a hard tissue implant material is disclosed to include inserting a stylet and cannula percutaneously and through the soft tissues of an organism until abutting hard tissue; further inserting the stylet into a predetermined location within the hard tissue; and ratcheting a pawl mechanism against a rack of gear teeth to advance the cannula along the stylet to the predetermined position.

Alternatively, a method of percutaneously implanting a hard tissue implant material includes inserting a stylet and cannula percutaneously and through the soft tissues of an organism until abutting hard tissue; further inserting the stylet into a predetermined location within the hard tissue; and rotating a camming mechanism associated with the stylet and cannula to apply a driving force against the cannula to advance the cannula along the stylet to the predetermined position.

In either case, the stylet preferably includes self-tapping threads extending from an end thereof, in which case the further insertion of the stylet into the hard tissue is accomplished by torquing the stylet to thread the self-tapping threads into and through the hard tissue.

Additionally, the methods include withdrawing the stylet from within the cannula while maintaining the cannula in the predetermined position the cannula may be connected to a source of implantable material wither after complete withdrawal of the stylet from within the cannula, or, alternatively, before the stylet has been completely withdrawn from the cannula.

BEST MODE FOR CARRYING OUT THE INVENTION

Figure 1:
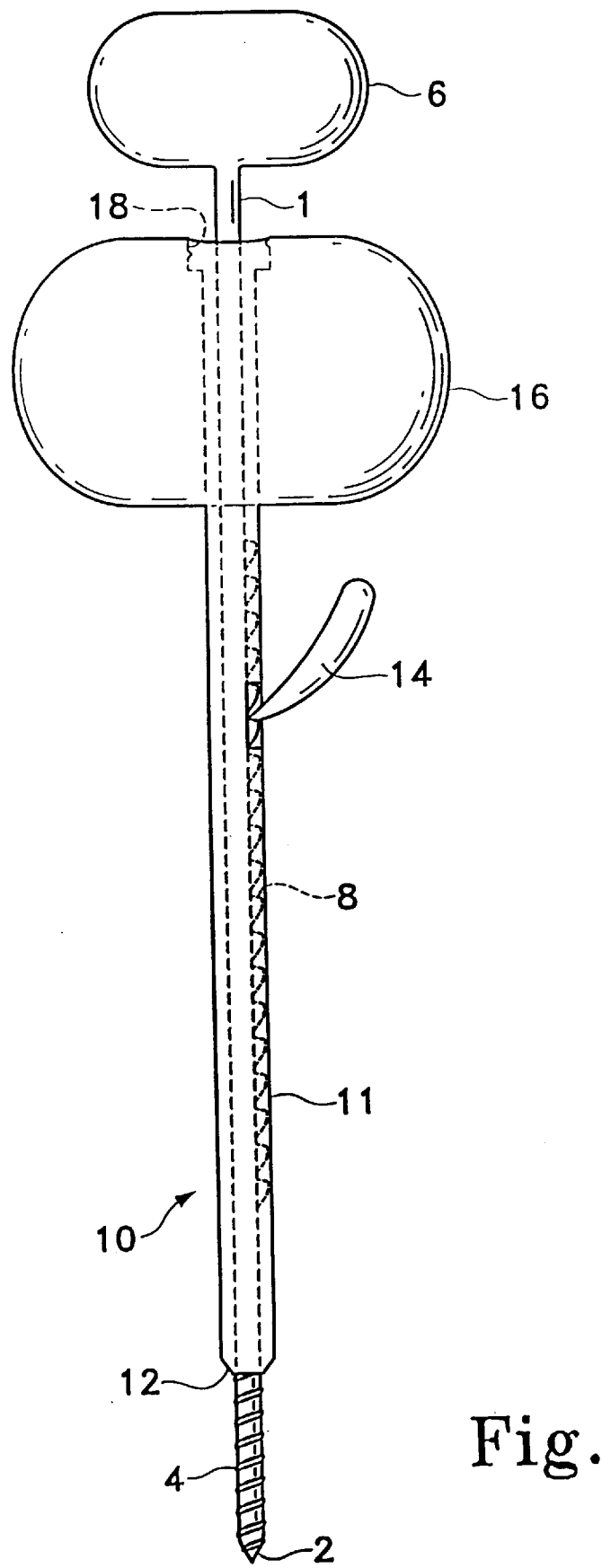
FIG. 1 is a plan view of a preferred embodiment of the depth guided cannula and stylet according to the present invention.

The present invention substantially reduces several of the risk factors associated with the performance of percutaneous vertebroplasty. Additionally, the present invention enables a reduction in the amount of pressure which must necessarily be applied to the cannula, as well as the "filler" to be implanted via the cannula.

As noted above, the general procedure for performing percutaneous vertebroplasty involves the use of a standard 11 gauge Jamshidi needle, illustrated as reference numeral 100 in the prior art illustration of FIGS. 8–11. The needle 100 includes an 11 gauge cannula 101 with an internal stylet 102. The cannula 101 and stylet 102 are used in conjunction to pierce the cutaneous layers of a patient above the hard tissue to be supplemented, then to penetrate the hard cortical bone 103 of the vertebra, and finally to traverse into the softer cancellous bone 104 underlying the cortical bone.

A large force F must be applied by the user, axially through the Jamshidi needle to drive the stylet 102 through the cortical bone 103. Once penetration of the cortical bone 103 (through the pedicle of the vertebra in this example) is achieved, additional downward axial force, but at a reduced magnitude compared to that required to penetrate the cortical bone, is required to position the stylet/tip of the cannula into the required position within the cancellous bone, as shown in a progression from FIG. 9 to FIG. 10. If the force magnitude is not reduced appropriately, or if very soft bone is encountered, as is often the case with osteoporitic patients, the stylet and cannula can be accidentally and suddenly driven through the cortical bone 103 on the opposite side of the vertebra. In one of the worse case scenarios, the stylet and cannula may continue traveling beyond the cortical bone and into the aorta 105, which is a potentially lethal situation. Another potential risk, due to the large driving forces required, is that the stylet 102 and cannula 101 could be driven askew and into the spinal cord 106 with the potential to cause permanent paralysis.

Because of the large forces required, it is not uncommon for the stylet and cannula to suddenly "break through" and make their pass through the cortical bone both very rapidly and very uncontrollably. Because of the speed with which such a break through can occur, it may be difficult if not impossible for the operator to react in time to reduce the driving force. Consequently, the cannula and stylet may be driven through the opposite cortical bone layer almost simultaneously.

The present invention overcomes these inherent risks by providing instruments, particularly cannulae, which can be driven through the cortical bone much more controllably and reliably. Less force is required to accomplish the placement of the instruments and, at the same time, the advancement of the instruments can be accomplished at a much slower and more controllable, consistent rate, e.g., as sequentially illustrated in FIGS. 12–17.

Turning to FIG. 1, a preferred example of depth guided instruments will now be described. A stylet 1 is provided which has a length that is more than sufficient to span the distance from the epidermis of a patient to the cancellous bone tissue in the vertebra, in the preferred configuration. Typically the length of the stylet would be about three inches or greater, but lesser lengths may also be employed as well, depending on the size of the patient. Of course, if other hard tissues are to be accessed, the length of the stylet can be readily modified without departing from the inventive features of the present invention.

The stylet 1 is preferably made of a surgical grade of stainless steel, but other known equivalent biocompatible metals and materials may be used for the same purpose. Ideally, the stylet, or at least a distal end thereof, will be radiopaque so that it can be monitored using fluoroscopy, CT or other imaging techniques during the procedure to help determine the depth and location of the penetration.

A first or distal end of the stylet 1 ends in a point 2 which is sharp and adapted to penetrate hard tissue when axially loaded. Preferably, although not necessarily, the stylet 1 includes self-tapping threads 4 extending from the tip 2. The self-tapping threads 4 provide an advantage in that once the tip 2 has penetrated the cortical bone (e.g., see FIG. 12), the operator of the stylet can than proceed to advance the stylet by torquing the stylet, which engages the self-tapping threads 4 in the cortical bone 103 and begins to screw the stylet 1 into the cortical bone. However, the stylet could, for example, use non-self tapping threads wherein a pre-tapped hole would be provided in the cortical bone prior to threading the stylet into position. Also, the stylet could have no threads whatsoever extending from the tip 2 and still employ the other advantageous features of the present invention.

The second or proximal end of the stylet preferably has a handle 6 molded or otherwise fixed thereto, to enable the operator to rotate or torque the stylet 1 about its longitudinal axis with a mechanical advantage, and also providing a surface against which to provide a pushing or axial force. The handle 6 is preferably molded of polycarbonate. However, any other materials which are durable, sterilizable and biofriendly, could be readily substituted. For example, the handle could be made from nylon or a host of other well-known plastics suitable for this purpose, or stainless steel, titanium, other biocompatible metals and ceramics.

A cannula 10 is provided which includes an elongated tubular structure 11 to be positioned in the cancellous bone for delivery of PMMA or other bone implant material therein. The tubular structure 11 of the cannula 10 is preferably made of a surgical grade of stainless steel, but may be made of known equivalent materials, similarly to the stylet 1 discussed above. Preferably, at least a distal end of the tubular structure is radiopaque. The tubular structure 11 has an inside diameter which is only slightly larger than the outside diameter of the stylet 1, so that the cannula may effortlessly pass axially over the stylet, while at the same time being supported and guided by the stylet. A first or distal end 12 of the cannula is preferably (but not necessarily) beveled to ease the penetration of the cannula through the cutaneous and soft tissues, and especially through the hard tissues.

A second or proximal end of the cannula preferably has a handle 16 molded or otherwise fixed thereto, to enable the operator to rotate, torque or push the cannula 10. The handle 16 is preferably molded of polyearbonate. However, any other materials which are durable, sterilizable and biofriendly, as discussed above with regard to handle 6, could be readily substituted.

The cannula 10 further includes a pawl 14 which extends through the wall of the cannula 11 and which can be ratcheted against a rack of gear teeth 8 provided on the stylet 1. Thus, the ratchet and pawl arrangement including pawl 14 and gear teeth 8 functions as a driving and control mechanism for the positioning, advancement and control of the cannula 10 with respect to the stylet I and vice versa. The pawl 14 can be ratcheted with respect to the rack 8 to move the cannula 10 up or down with respect to the stylet 1.

When a stylet is to be threaded or otherwise turned into position for guiding the cannula 10, the stylet may include gear teeth that cicrumscribe the stylet shaft so that the gear teeth are never out of alignment with the pawl 14 on the cannula 10, regardless of the rotational position of the stylet with respect to the cannula.

Figure 12:
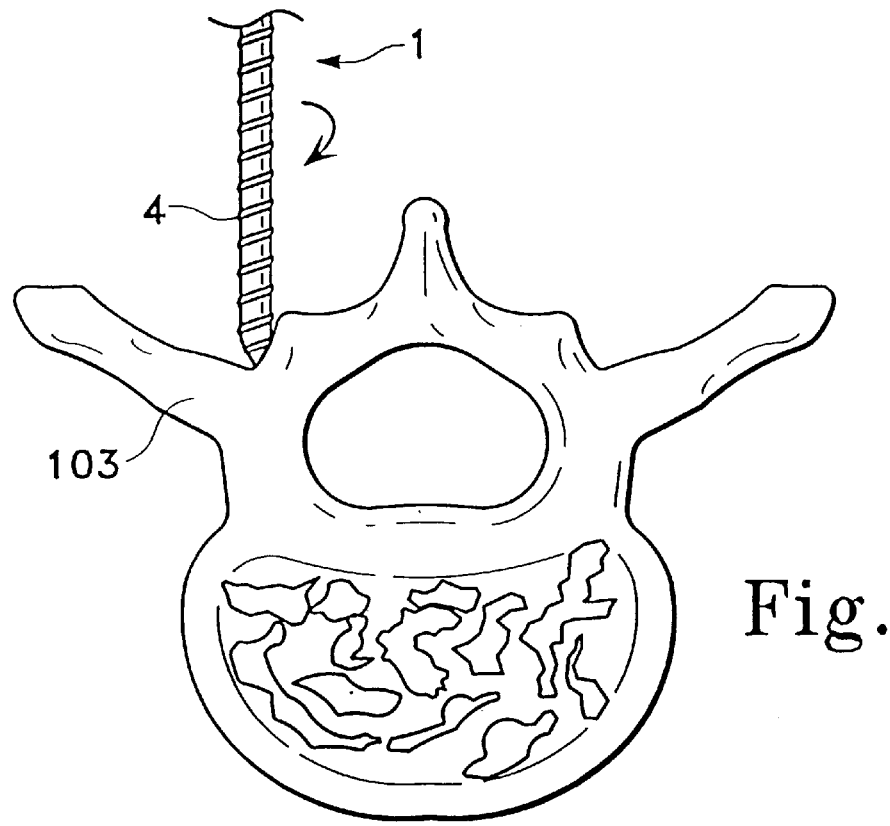
FIGS. 12, 13, 14, 15, 16 and 17 illustrate some of the advantages and risk reduction that are inherent in using the present invention.
Figure 13:
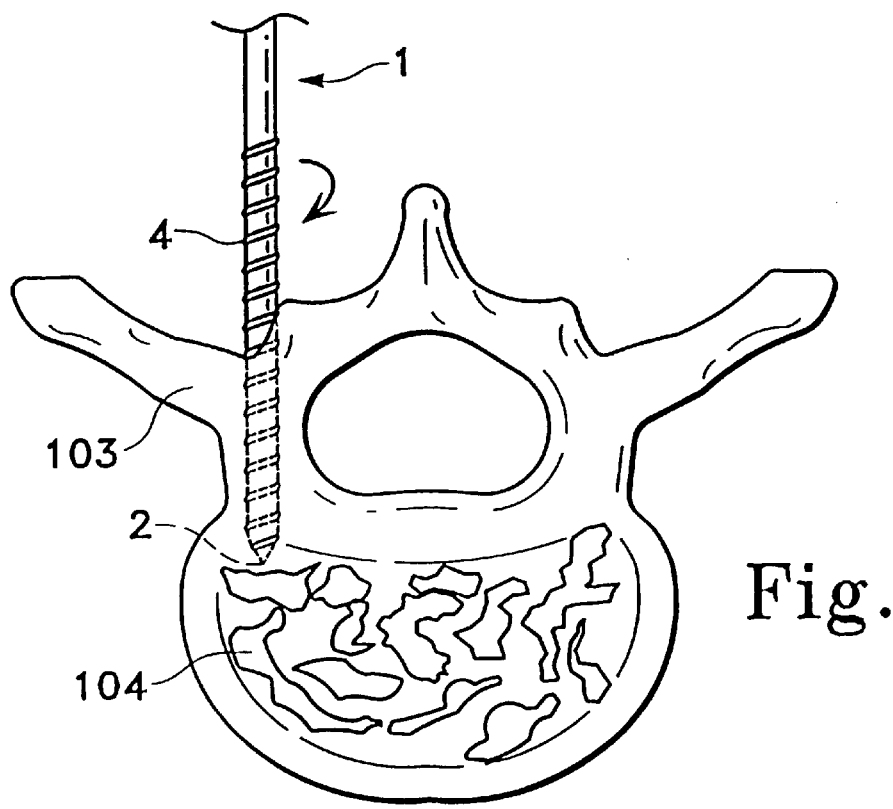
Figure 14:
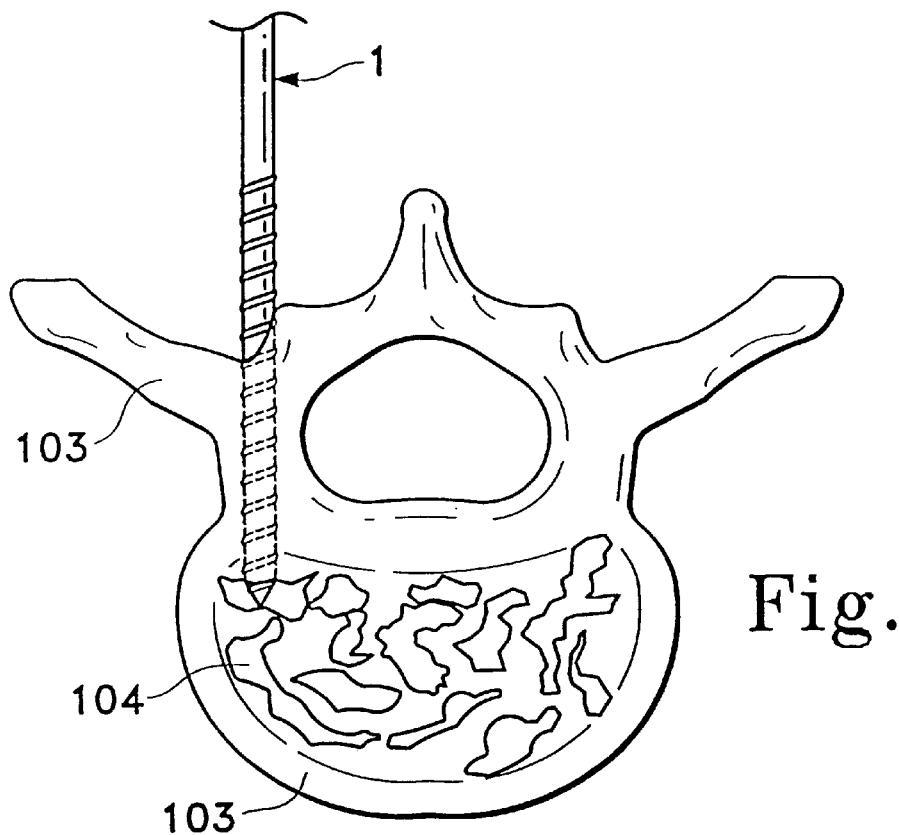

After screwing the stylet 1 into the desired position (e.g., the cancellous tissue of the vertebra as shown in FIGS. 12–14) in the hard tissue, as confirmed by viewing the position using an imaging technique referred to above, the operator proceeds to grasp the handle 6 so as to prevent the stylet from rotating further.

Figure 15:
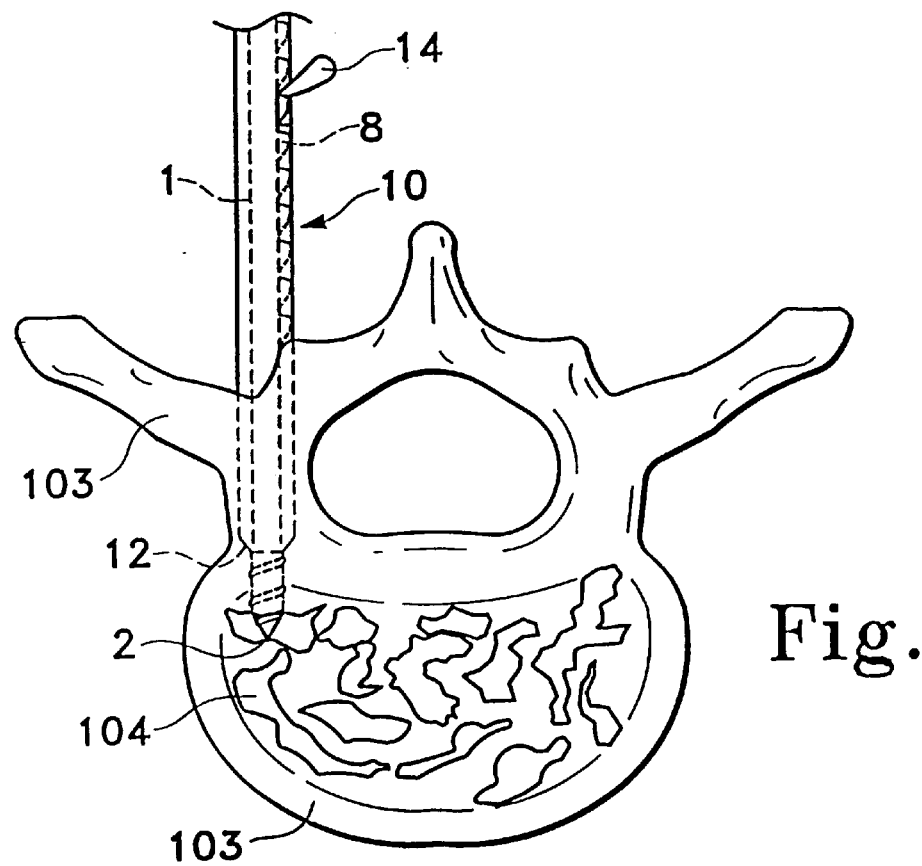
Figure 16:
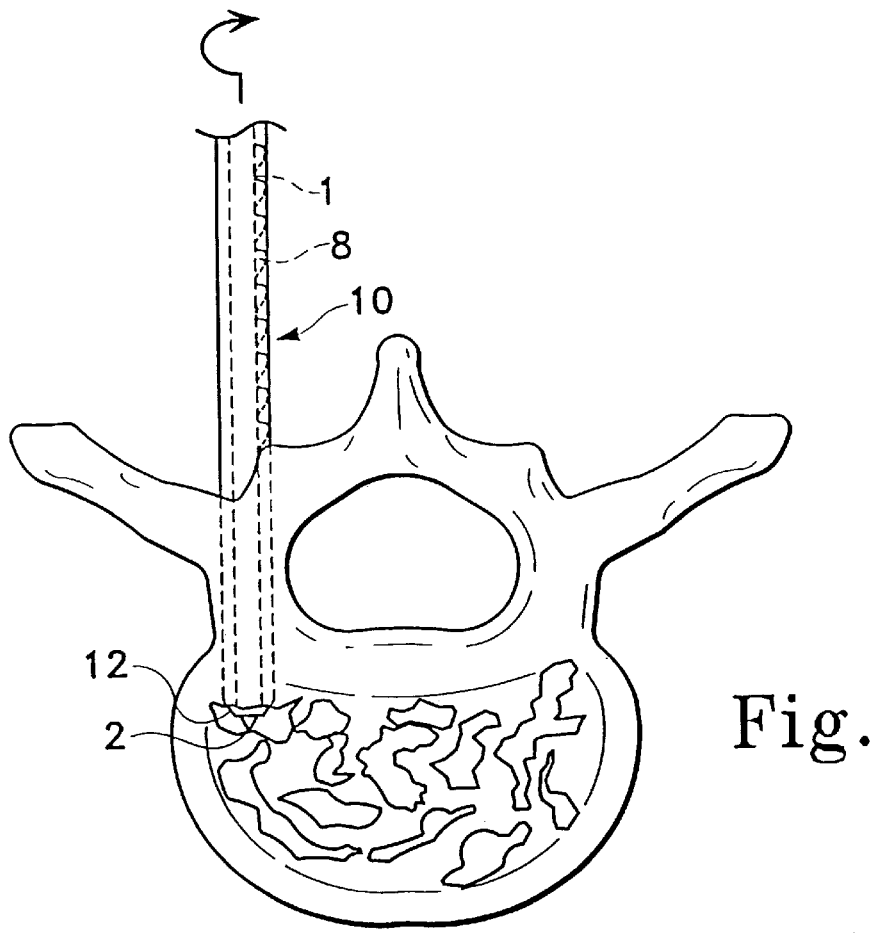

At the same time, the operator would ratchet the pawl 14 in an up and down fashion to advance the beveled end 12 of the cannula in a direction toward the point of the stylet 2 (FIG. 15). The advancement of the cannula 10, and particularly the beveled end 12 are monitored using an imaging technique to ensure the proper placement of the cannula for injection of the PMMA or other hard tissue implant material. When the beveled end 12 is advanced to a position that is substantially flush with point 2 (FIG. 16), the operator will cease the advancement of the cannula 10, since it will have reached its optimal position.

Figure 17:
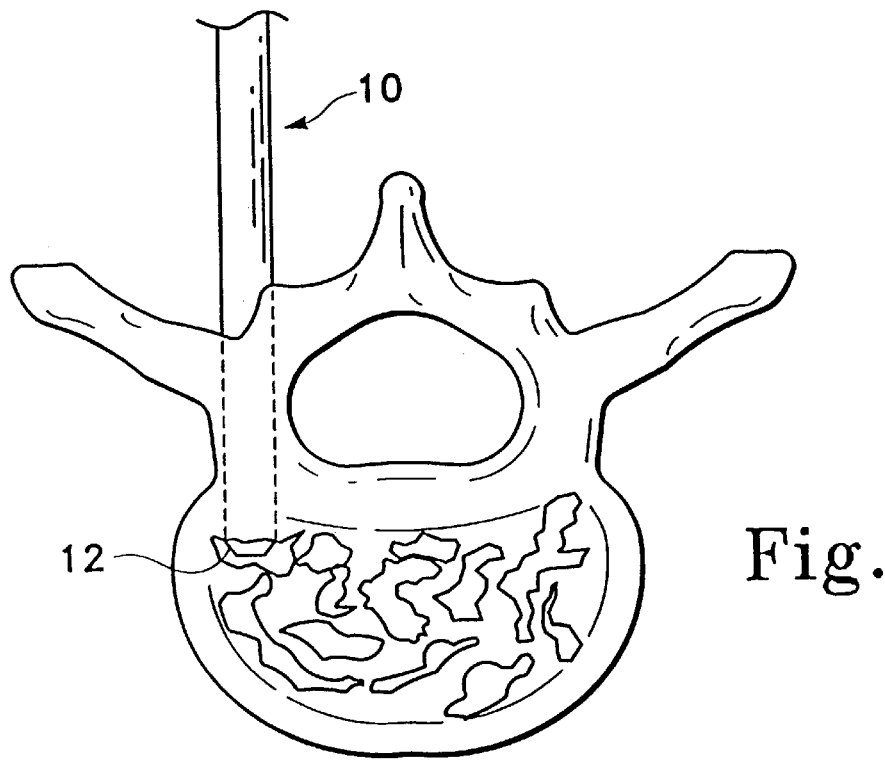

Upon disengaging the pawl 14 from the rack 8, the stylet 1 can then be reverse rotated out of the bone and then slid out from its position within the cannula 10, while maintaining the cannula 10 in its position, as shown in FIG. 17.

An alternative method of inserting the cannula 10 would be to incrementally insert the stylet 1 and the cannula 10. More specifically, the operator would advance the stylet 1 only partially into the cortical bone 103 of the pedicle, and then advance the cannula 10 so as to be substantially flush or close to the tip 2, by ratcheting as described above. Then the operator would again advance the stylet 1 for a small distance through the cortical bone, stop the advancement and follow with advancement of the cannula 10 by the same increment. This type of incremental advancement could be continued until the tip 2 and the beveled end reach the same desired location as described above and shown in FIG. 16. Incremental advancement may still further reduce the force that is necessary to be applied to advance the cannula 10 through the cortical bone 103. However, the incremental approach is more time consuming, which is a factor that must be considered in deciding whether or not to use the incremental approach.

Surrounding the second end of the tubular structure 11 is a connector 18 for linking the cannula 10 with a syringe or other tubular supply, for supplying the PMMA or other implantable material that is to be injected via tubular structure 11. Preferably, connector 18 is a Luer-lock type of connector, but other known connecting mechanisms may be successfully interchanged, e.g., a conventional threaded hole, a threads and locking nut arrangement, etc.

Figure 2:
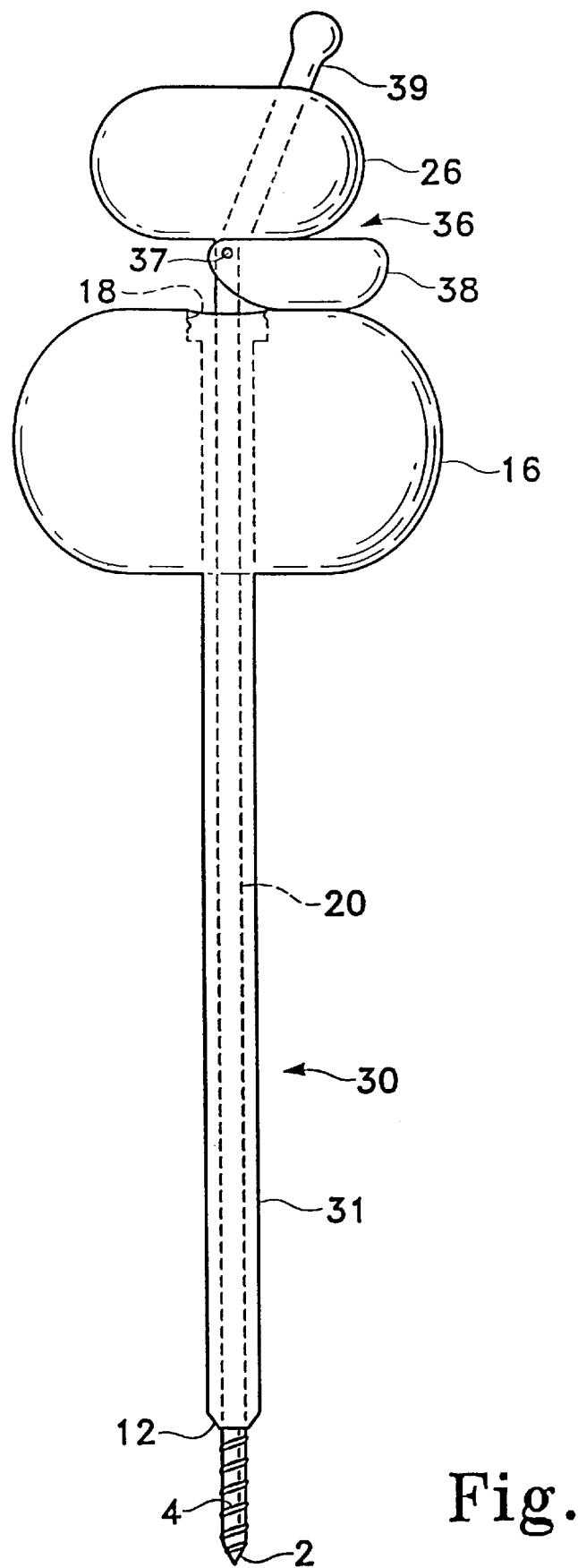
FIG. 2 is a plan view of another embodiment of a depth guided cannula and stylet according to the present invention.

FIG. 2 illustrates an alternative embodiment of a stylet 20 and cannula 30 for uses similar to those described with the embodiment shown in FIG. 1. Stylet 20 includes a tip 2 and preferably, but not necessarily, self-tapping threads 4, just as in the embodiment of FIG. 1. The materials employed to make the devices in FIG. 2 are the same as those discussed above with regard to like parts in FIG. 1.

The second or proximal end of the stylet 20 has a handle 26 molded, threaded or otherwise fixed thereto, to enable the operator to torque the stylet about its longitudinal axis with a force applied through a mechanical advantage, and to enable the operator to apply axial force to the stylet. Cannula 30 is provided and includes an elongated tubular structure 31 for positioning in the cancellous bone for delivery of PMMA or other bone implant material therein. The tubular structure 31 has an inside diameter which is only slightly larger than the outside diameter of the stylet 20, so that the cannula may effortlessly pass axially over the stylet, while at the same time being supported and guided by the stylet. A first or distal end 12 of the cannula is preferably (but not necessarily) beveled to ease the penetration of the cannula through the cutaneous and soft tissues, and especially through the hard tissues.

A second or proximal end of the cannula preferably has a handle 16 molded, threaded or otherwise fixed thereto, to enable the operator to rotate, torque or push the cannula 30.

A driving mechanism 36 is pivotally mounted to the stylet 20 va pin 37. At least one cam lobe 38 is positioned between handles 26 and 16 for application of force to handle 16 upon actuation. As shown in FIG. 4, the driving mechanism preferably includes a pair of cam lobes located on opposite sides of the stylet shaft. Handle 26 is provided with a slot 35 which receives lever 39 therein. Lever 39 is rotatable about the pivot 37 to apply a rotational force to cam mechanism 38. Upon rotation of lever 39 from the position shown in FIG. 2 to the position shown in FIG. 3, the camming surface of cam mechanism 38 provides a driving force to drive cannula 20 from a first position shown in FIG. 2 to a second position shown in FIG. 3, where the end 12 of the cannula is substantially flush with the tip 2 of the stylet.

Figure 3:
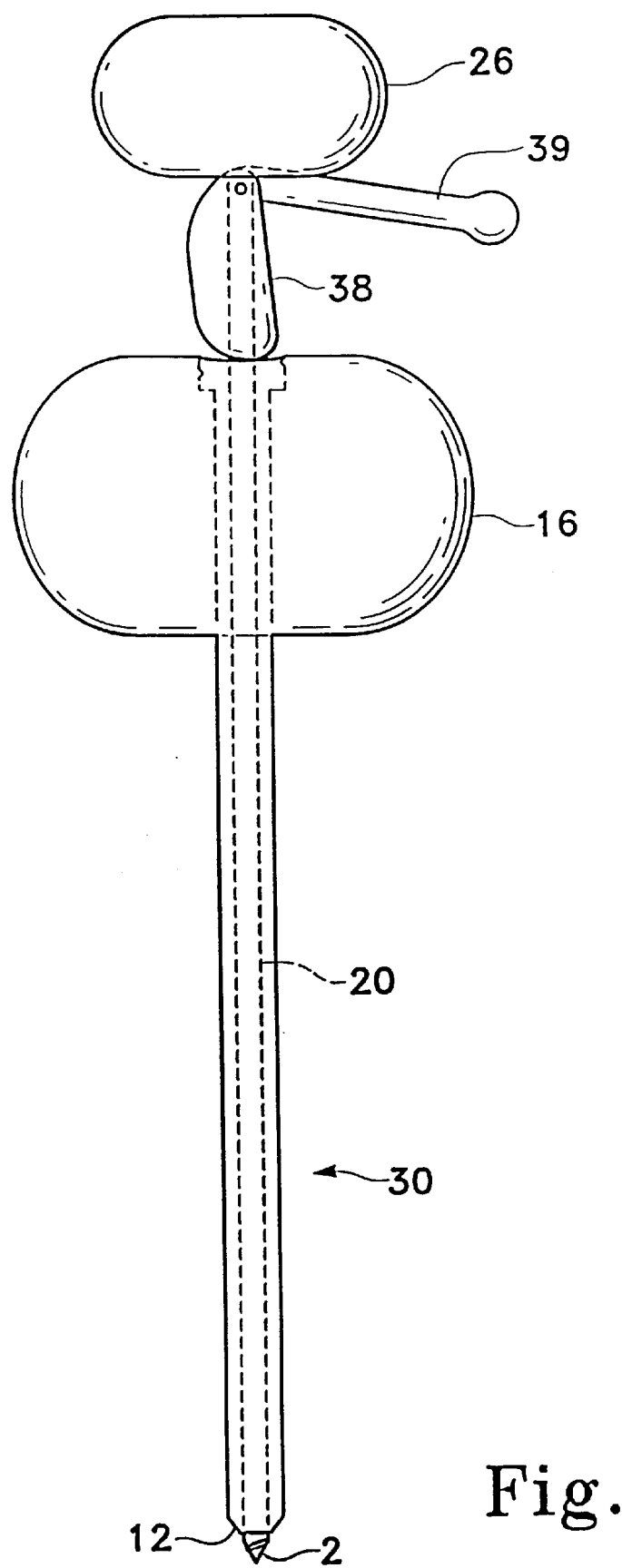
FIG. 3 is an additional view of the invention shown in FIG. 2, with the cannula in a second preset position with respect to the stylet.
Figure 4:
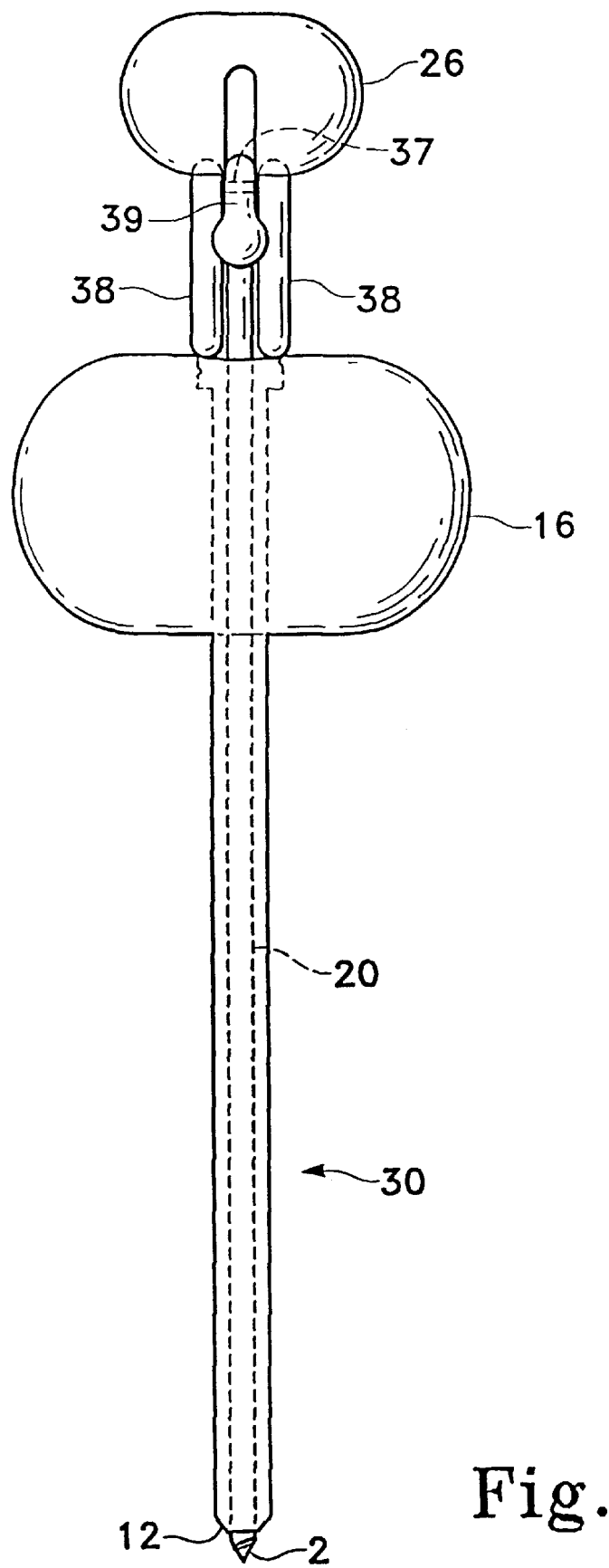
FIG. 4 is yet another view of the embodiment shown in FIGS. 2–3, with the instruments having been rotated about their longitudinal axes by about ninety degrees.

It is noted that both the embodiments of FIGS. 1 and 2 can be configured so that, when using a stylet having end threads, self-tapping or otherwise, the selftapping may be covered to enables the stylet and cannula to be pushed through the soft tissues of the patient with less drag and less damage to the soft tissues of the patient than would result if the tapping threads were exposed during this part of the procedure e.g., see the configuration shown in FIG. 3.

Once the stylet tip 2 has penetrated the cortical bone, the operator can then retract the cannula 10, 30 from the tip 2 to expose the threads 4 to be threaded into the bone. For this step, it is noted that retraction of the embodiment in FIG. 2 is much faster than that of FIG. 1, requiring only a simple rotation of handle 39 as compared to a significant amount of ratcheting of the pawl 14.

Once in the preset position shown respectively in FIGS. 1 and 2, the stylet is configured to be passed through the cortical bone and into the desired position, either by the use of self-tapping threads 4 or other means discussed above, including simply piercing an unthreaded stylet through the cortical bone. When threads are used, handle 26 is next torqued in a clockwise direction to engage the self-tapping threads 4 in the cortical bone and begin screwing the stylet 1, 20 through the cortical bone and into the desired position in the cancellous bone. After screwing the stylet 1, 20 into the desired position (e.g., the cancellous tissue of the vertebra) in the hard tissue, as confirmed by viewing the position using an imaging technique referred to above, the operator proceeds to move the cannula 10, 30 into position in the manners already described.

Although the use of a stylet having no threads for threading into the bone does not provide the same measure of safety and control for advancement of the stylet, the embodiments of FIGS. 1 and 2 would still provide substantially the same factors of safety for advancement of the respective cannulae disclosed therein.

Similar to the above description with regard to the embodiment in FIG. 1, an alternative method of inserting the cannula 30 would be to incrementally insert the stylet 20 and the cannula 30. More specifically, the operator could thread or otherwise insert the stylet 20 only partially into the cortical bone 103 of the pedicle, and then advance the cannula 30 so as to be substantially flush or close to the tip 2 as described above. Then the operator would release the camming surface 38 to position lever 39 as shown in FIG. 2, and then again advance the stylet for a small distance through the cortical bone, stop the advancement and follow with advancement of the cannula 30 by the same increment. This type of incremental advancement could be continued until the tip 2 and the beveled end reach the same desired location as described above. Incremental advancement may still further reduce the force that is necessary to be applied to advance the cannula 30 through the cortical bone 103 and thereby increase the safety factor during insertion of the cannula 30. However, the incremental approach is more time consuming, which is a factor that must be considered in deciding whether or not to use the incremental approach.

Surrounding the second end of the tubular structure 31 is a connector 18 for linking the cannula 30 with a syringe or other tubular supply, for supplying the PMMA or other implantable material that is to be injected via the tubular structure 31.

Figure 5:
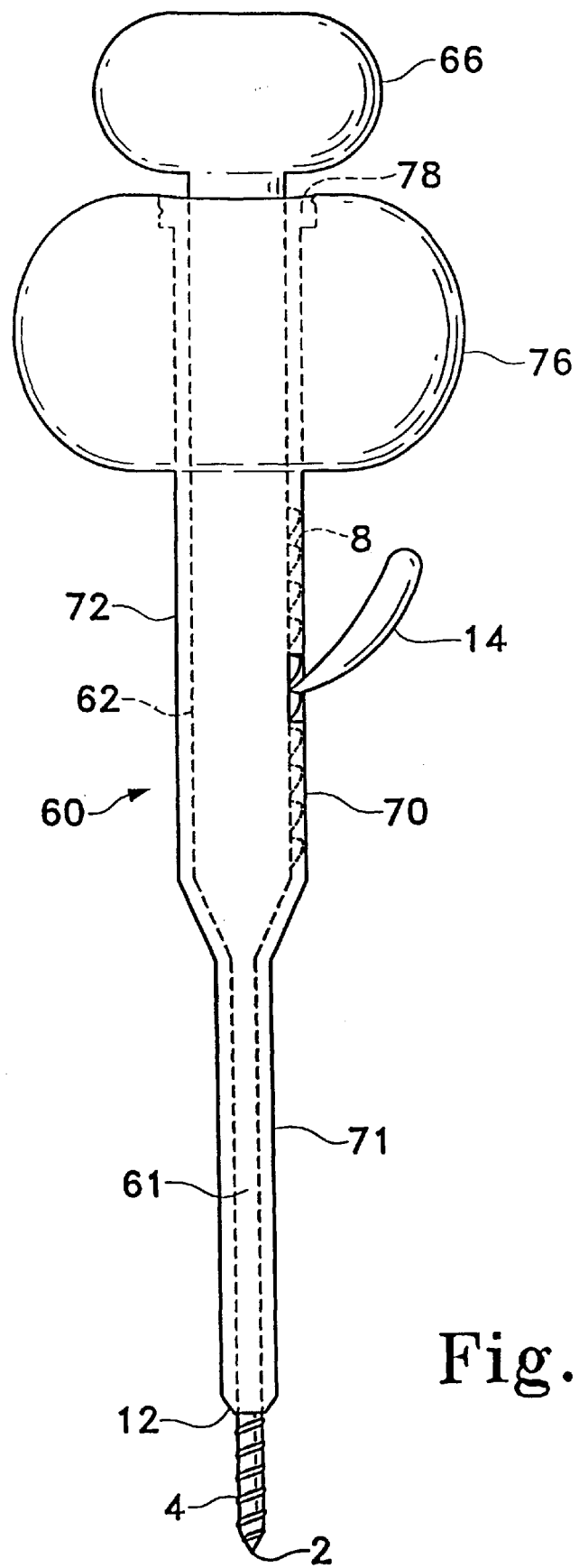
FIG. 5 shows another preferred embodiment according to the present invention which employs a pressure reduction feature.

FIG. 5 shows a variant of the embodiment described with regard to FIG. 1. In order to reduce the substantial amount of pressure that is required to inject PMMA or other bone filler through a standard sized cannula, FIG. 5 shows a modification in which the cannula 70 includes a modified tubular structure design. The first or distal portion 71 of the tubular structure is of the same dimensions as the embodiment of FIG. 1. The second or proximal portion 72 of the cannula 70, however, has a substantially larger diameter than that of the first portion 71. Preferably, the diameter of second portion 72 is about twice the diameter of first portion 71, although any increase in the diameter of second portion 72 over that of the first portion 71 will decrease the pressure requirement for effective delivery of the material to be implanted.

The first and second portions 71, 72 have approximately equal lengths, but this is governed by the anatomy of the site to be accessed. In the "average" percutaneous vertebroplasty situation, the first portion 71 is required to be about 1.5" long, as this is the length that is needed for traversing the cortical bone of the pedicle. Thus, the first portion should not be significantly enlarged due to the size constraints of the pedicle, the safety risks to the spinal column and aorta which are increased when the cannula size is increased intravertebrally, and by the desire to remove as little bone as possible when entering with the stylet and cannula, among other factors.

However, the portion of the cannula which will occupy the soft tissues can be significantly expanded without substantially adversely effecting the patient. Given the benefits of reducing the required injection pressure and ensuring a better delivery of the bone implant material, such a modification becomes a viable option.

The devices shown in FIG. 5 operate similarly to that of the embodiment of FIG. 1, i.e., a pawl 14 passes through a wall of the cannula 70, preferably in the second portion 72. The pawl 14 can be ratcheted against a rack of gear teeth 8 provided on the stylet 60. Thus, the ratchet and pawl arrangement including pawl 14 and gear teeth 8 functions as a driving and control mechanism for the positioning, advancement and control of the cannula 70 with respect to the stylet 60 and vice versa. The pawl 14 can be ratcheted with respect to the rack 8 to move the cannula 70 up or down with respect to the stylet 60.

When a stylet is to be threaded or otherwise turned into position for guiding the cannula 10, the stylet may include gear teeth that cicrumscribe the stylet shaft so that the gear teeth are never out of alignment with the pawl 14 on the cannula 10, regardless of the rotational position of the stylet with respect to the cannula. In the embodiment shown in FIG. 5, the stylet 60 is designed to closely follow the contour of the cannula 70 to provide a close guidance along the full length of the cannula 70. While the first portion 61 is substantially of the same diameter as the stylet 1 in FIG. 1, the second portion 62 must be substantially larger, preferably twice the diameter of the first portion, to follow the contours of the portion 72 of the cannula. However, a stylet having only a single diameter throughout, e.g., a diameter equal to that of portion 61 could be employed. Such an embodiment would require modification of the pawl 14 to extend further radially inward so as to interact with gear teeth that would be placed on a smaller diameter stylet. Similar to the embodiment of FIG. 1, the ratcheting of the pawl against gear teeth 8 provides a driving and control mechanism for the positioning, advancement and control of the cannula 70 with respect to the stylet 60 and vice versa.

Handle 76 is substantially similar to handle 16 in its design, material, and connection with the tubular structure 71. However, due to the increased diameter of the second portion 72 of the tubular structure 70 and the second portion 62 of the stylet 60, the handle 76 must also have an increased hole through which the second portion 62 of the stylet 60 passes. Handle 66 is substantially similar to handle 6 in its design, material, and connection with the stylet 60, although if molded around the stylet 60, the handle 66 must also have a larger hole than handle 6 to pass the enlarge diameter of the stylet portion 62.

Surrounding the second end of the tubular structure of the cannula 70 is a connector 78 for linking the cannula 70 with a syringe or other tubular supply, for supplying the PMMA or other implantable material that is to be injected via the cannula 70. Preferably, connector 78 is a Luer-lock type of connector, but other known connecting mechanisms may be successfully interchanged, e.g., a conventional threaded hole, a threads and locking nut arrangement, etc.

Figure 6:
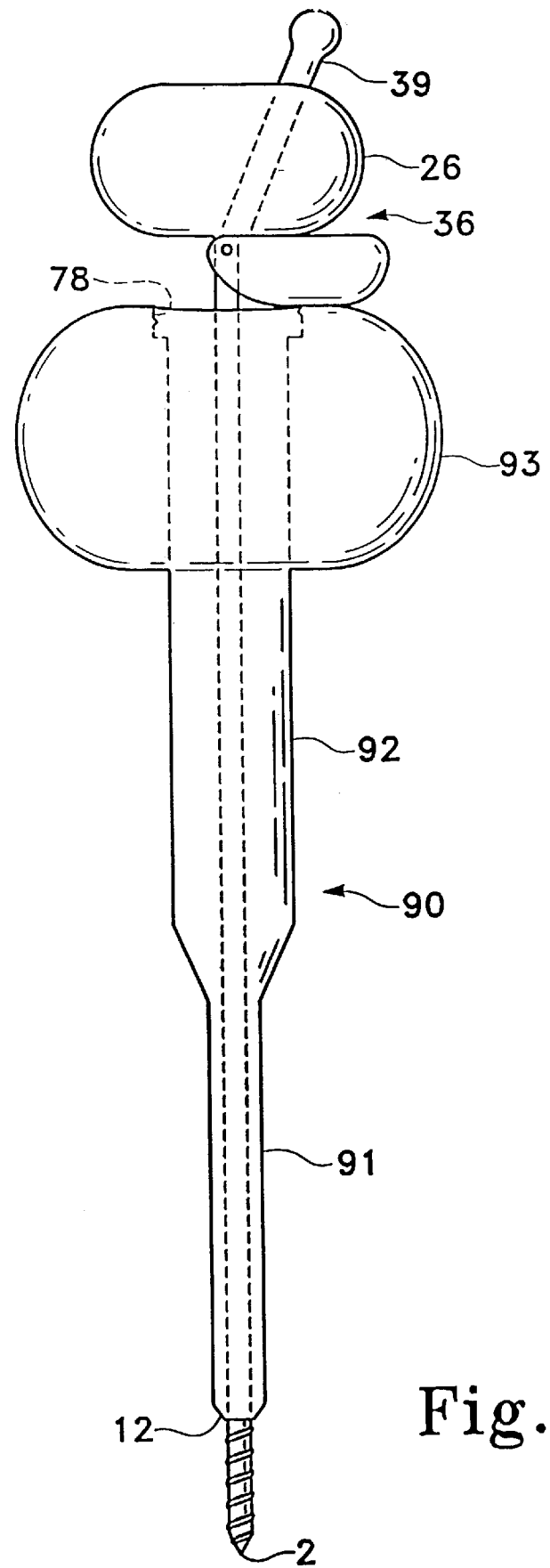
FIG. 6 shows another embodiment according to the present invention which employs a pressure reduction feature.

The variant shown in FIG. 6 combines the advantages of the embodiment shown in FIGS. 2–4 with the pressure reducing concept described above with respect to FIG. 5. The variant shown in FIG. 6 uses the same stylet 20 as that shown in FIG. 2, but has a cannula 90 which includes a modified tubular structure design. However, a stylet that generally follows the contours of cannula 90 could alternatively be used. The first or distal portion 91 of the tubular structure is of the same dimensions as the cannula 30. The second or proximal portion 92 of the cannula 90, however, has a substantially larger diameter than that of the first portion 91, similar to the cannula in FIG. 5. Preferably, the diameter of second portion 92 is about twice the diameter of first portion 91, although any increase in the diameter of second portion 92 over that of the first portion 91 will decrease the pressure requirement for effective delivery of the material to be implanted.

The devices shown in FIG. 6 operate similarly to that of the embodiment of FIGS. 2–5 with the added advantage of reduction of the pressure required to deliver the implant material.

Handle 93 is substantially similar to handle 16 in its design, material, and connection with the tubular structure 92. However, due to the increased diameter of the second portion 92 of the tubular structure 90, the handle 93 must also have an increased hole through which the second portion 92 of the cannula 90 passes.

Surrounding the second end of the tubular structure of the cannula 90 is a connector 78 for linking the cannula 90 with a syringe or other tubular supply, for supplying the PMMA or other implantable material that is to be injected via the cannula 90. Preferably, connector 78 is a Luer-lock type of connector, but other known connecting mechanisms may be successfully interchanged, e.g., a conventional threaded hole, a threads and locking nut arrangement, etc. The driving control mechanism functions essentially the same as that described above with regard to FIGS. 2–4.

Figure 7:
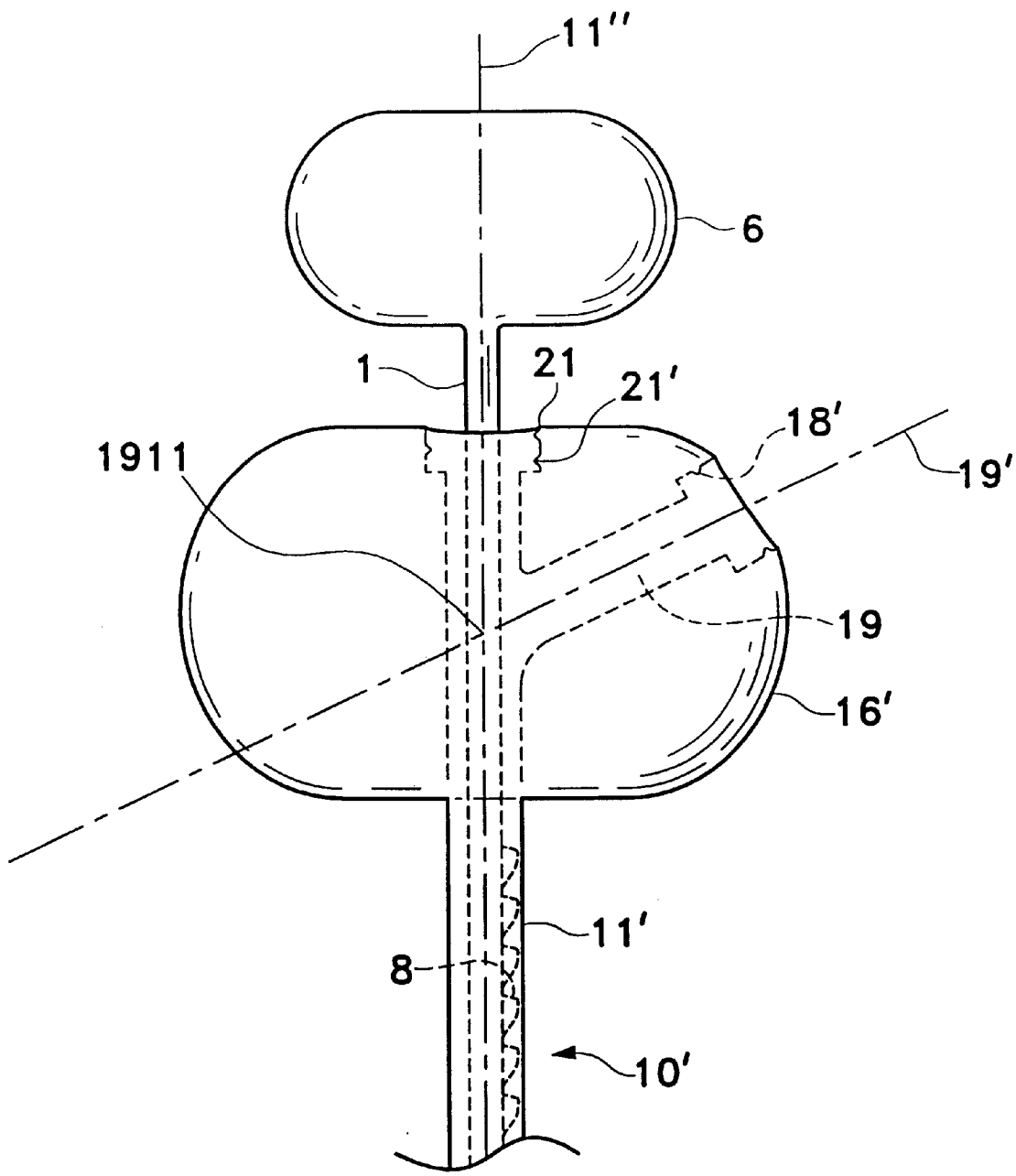
FIG. 7 shows a variant of a connector placement according to the present invention.
Figure 8:
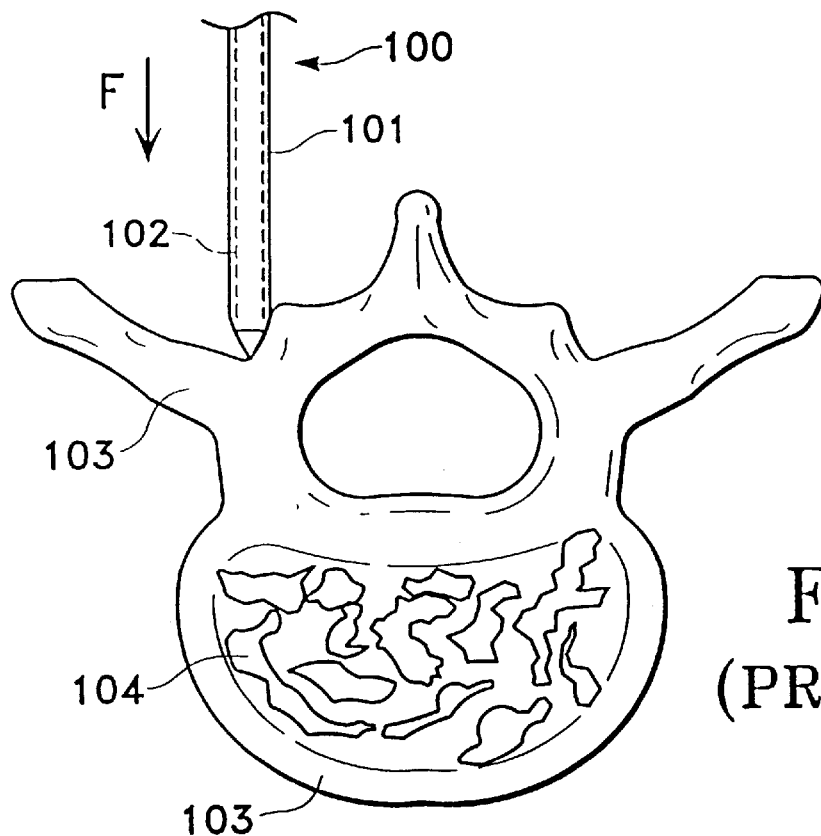
FIGS. 8, 9, 10 and 11 are progressive views illustrating one of the more serious risks involved in a prior art procedure.
Figure 9:
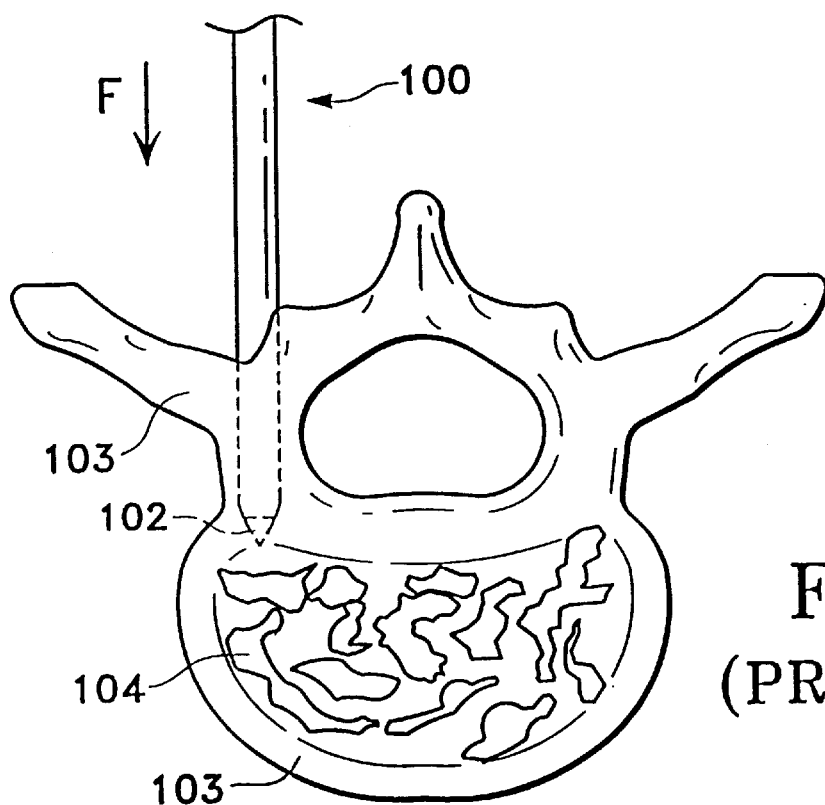
Figure 10:
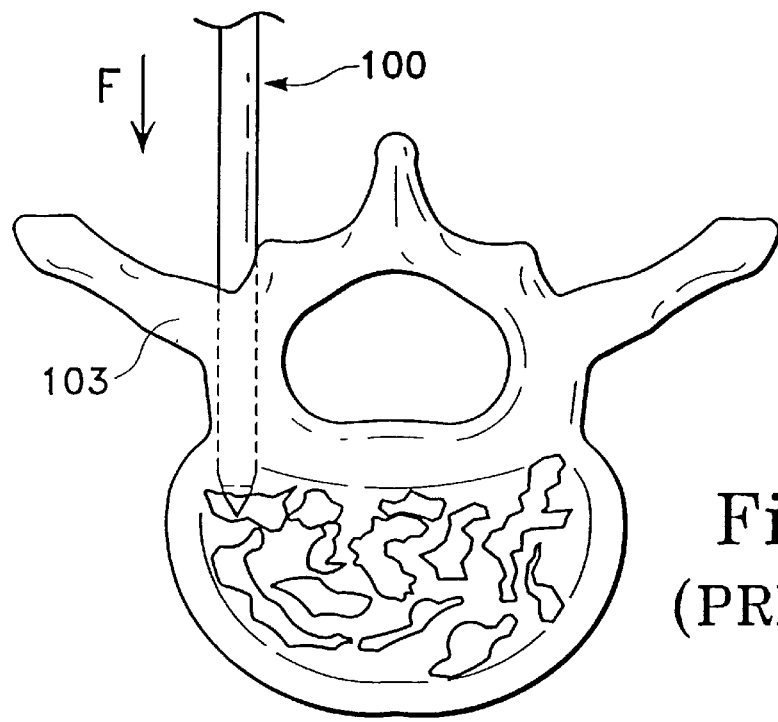
Figure 11:
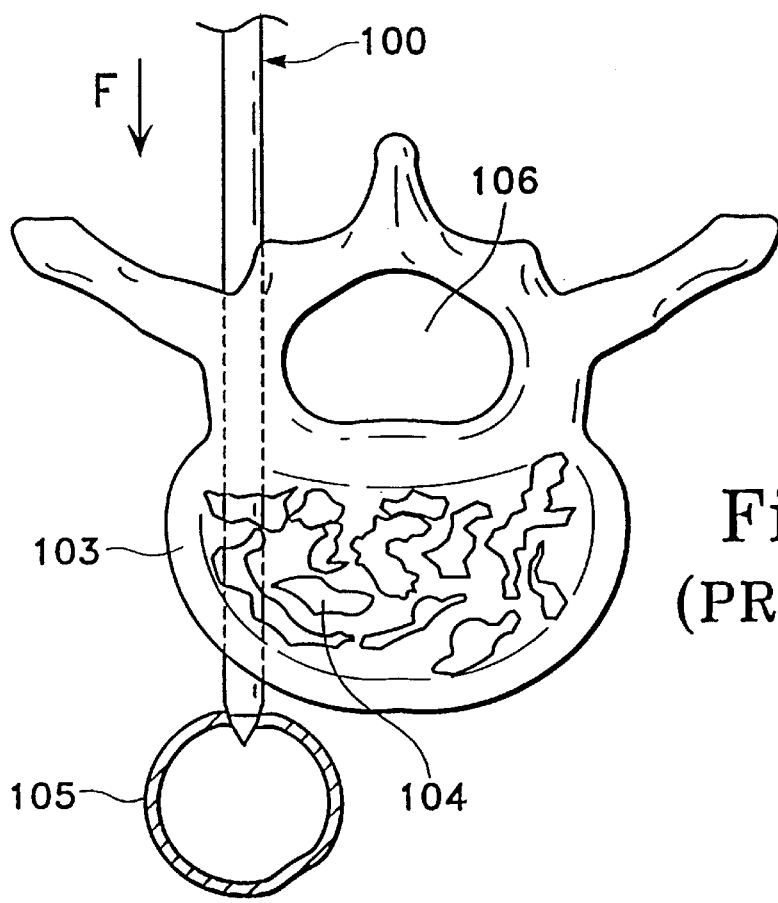

FIG. 7 shows a variation in the placement of a connector 18' for linking the cannula 10' with a syringe or other tubular supply, for supplying the PMMA or other implantable material that is to be injected via tubular structure 11'. This variation can also be employed with any of the earlier described cannula embodiments. Preferably, connector 18' is a Luer-lock type of connector, but other known connecting mechanisms may be successfully interchanged, e.g., a conventional threaded hole, a threads and locking nut arrangement, etc.

In this variant, the connector 18' is provided on the surface of handle 16' at a position out of line with the longitudinal axis 11 of the cannula 11'. Thus, an additional bore 19 is provided in handle 16' to join the connector 18' with the internal bore of the cannula 10' such that longitudinal axis 19' of bore 19 is non-parallel with and intersects longitudinal axis 11" of cannula 11' at imaginary intersection point 1911. The connector 18' may be positioned at any convenient angle to the longitudinal axis of the cannula 11' and located at any convenient location on the surface of handle 16'. This variation enables pressure to be applied, and even the beginning of injection of the implant material, while the stylet 1 is still at least partially inserted within the cannula 11'. Additionally, this arrangement would allow the bore 19 to be of a significantly larger diameter than the bore of the cannula 10' to give an even further reduction in the amount of pressure that need be applied to implant the implantable material. A seal 21 (e.g., an o-ring or equivalent) may be provided to help maintain a pressure seal between the stylet 1 and the handle 16' in the event that the stylet 1 is still within the handle 16' when injection begins. Additionally or alternatively, threads 21' may be provided in handle 16' to accept a plug to positively seal the handle 16' during injection.

Although there have been described above a specific arrangement of devices for percutaneous delivery of a bone implant material, with a limited selected number of alternative embodiments in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as set forth in the claims which follow.

What is claimed is:

1. A stylet, comprising:
   an elongated rod having first and second ends and a longitudinal axis, said first end terminating in a point adapted for piercing hard tissue; and
   a camming mechanism pivotally mounted to provide a driving force to a cannula upon pivoting said camming mechanism with respect to said elongated rod.

2. The stylet of claim 1, further comprising a handle attached to said second end of said elongated rod.

3. The stylet of claim 1, further comprising:
   self-tapping threads extending from said point along said elongated rod for a predetermined distance, said self-tapping threads adapted to self-tap into hard tissue.

4. A kit adapted to open a pathway into hard tissue, comprising:
   a depth guided stylet comprising:
   an elongated rod having first and second ends and a longitudinal axis, said first end terminating in a point adapted for piercing hard tissue; and a camming mechanism pivotally mounted to provide a driving force to a cannula upon pivoting said camming mechanism with respect to said elongated rod; and a cannula comprising:

an elongated tube having first and second ends, said first and second ends being open and adapted for said depth guided stylet to pass therethrough; and a surface adapted to interact with said camming mechanism for the transfer of said driving force.

5. The kit of claim 4, further comprising:

self-tapping threads extending from said point along said elongated rod for a predetermined distance, said self-tapping threads adapted to self-tap into hard tissue.

6. The kit of claim 4, wherein said depth guided stylet further comprises a handle provided on said second end for providing a mechanical advantage to a user in rotating said elongated rod about said longitudinal axis.

7. The kit of claim 4, wherein said cannula further comprises a handle provided on said second end of said elongated tube, said surface being located on said handle of said cannula.

8. The kit of claim 7, further comprising a connector on said handle for connecting said cannula to tubing following removal of said stylet from within said cannula.

9. The kit of claim 8, wherein said connector comprise a Luer lock fitting.

10. The kit of claim 8, further comprising a bore through at least a portion of said handle, said bore connecting said connector with said elongated tube.

11. The kit of claim 10, wherein a longitudinal axis of said bore is non-parallel with and intersects a longitudinal axis of said elongated tube.

12. The kit of claim 4, wherein said elongated tube comprises a first section having a first diameter, and a second section having a second diameter larger than said first diameter; and wherein said first section is closer than said second section to said first end of said elongated tube.

13. The kit of claim 12, wherein said elongated rod comprises a first rod section having a first rod diameter, and a second rod section having a second rod diameter larger than said first rod diameter.

14. A stylet, comprising:

an elongated rod having first and second ends and a longitudinal axis, said first end terminating in a point adapted for piercing hard tissue;

threads extending from said point along said elongated rod for a predetermined distance; and means for biasing said elongated rod with respect to a cannula, in a direction of said longitudinal axis, said means for biasing being movable from a first position, at which said elongated rod extends from an end of the cannula to allow said threads to engage tissue; and a second position, at which said cannula covers substantially all of said threads.

15. A kit adapted to open a pathway into hard tissue, comprising:

a depth guided stylet comprising:

an elongated rod having first and second ends and a longitudinal axis, said first end terminating in a point adapted for piercing hard tissue; and threads extending from said point along said elongated rod for a predetermined distance;

a cannula comprising:

an elongated tube having first and second ends, said first and second ends being open and adapted for said elongated rod to pass therethrough; and means for biasing said cannula, in a direction of said longitudinal axis, with respect to said stylet, said means for biasing being movable from a first position, at which said elongated rod extends from an end of the cannula to allow said threads to engage tissue; and a second position, at which said cannula covers substantially all of said threads.

* * * * *